United States Patent [19]

Holan et al.

[11] Patent Number: 4,474,815
[45] Date of Patent: Oct. 2, 1984

[54] INSECTICIDAL OXIMES

[75] Inventors: George Holan, Brighton; Wynona M. P. Johnson, Bentleigh, both of Australia

[73] Assignee: Commonwealth Scientific and Industrial Research Organization, Campbell, Australia

[21] Appl. No.: 370,971

[22] Filed: Apr. 2, 1982

[30] Foreign Application Priority Data

Apr. 30, 1981 [AU] Australia ............................... PE8653

[51] Int. Cl.$^3$ ..................... A61K 31/15; C07C 131/00
[52] U.S. Cl. .................................. 424/327; 564/256; 549/442
[58] Field of Search ..................... 564/256; 424/327; 549/442

[56] References Cited

FOREIGN PATENT DOCUMENTS 7945234 3/1979 Australia .

Primary Examiner—Natalie Trousof
Assistant Examiner—L. Hendriksen
Attorney, Agent, or Firm—Bacon & Thomas

[57] ABSTRACT

Compounds of the general formula (I)

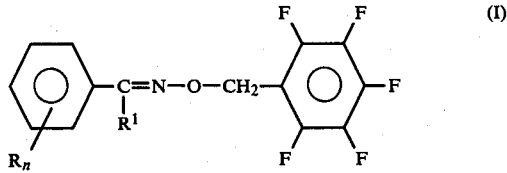

wherein
R represents F, Cl, Br, I, ethoxy, methoxy or propoxy and n is an integer between 1 and 5; or
R represents 3,4-methylenedioxy; and
R$^1$ represents di- or tri-chloromethyl.

The compounds have arthropodicidal (especially insecticidal and acaricidal) activity.

15 Claims, No Drawings

INSECTICIDAL OXIMES

The invention relates to new O-pentafluorobenzyl ethers of oximes of substituted phenyl halomethyl ketones, to a process for their preparation and to their use as arthropodicides, especially as insecticides and acaricides.

Reference has been made in the literature to a general class of alkyl aryl ketone oxime ethers of the general structure

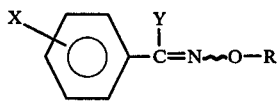

wherein X is one or more substituents, Y is an alkyl group and R-OH is the alcohol component of active pyrethroid esters (Michael J. Bull et al., *Pesticide Science*, 1980, 11, 249–256). The same reference discloses specifically a limited group of compounds falling within the broad class in which X is 4-chloro, 4-fluoro or 4-methoxy, Y is methyl, ethyl, isopropyl, cyclopropyl or cyclobutyl and R is 3-phenoxybenzyl. Some of these compounds showed insecticidal activity. U.S. Pat. No. 4,079,149 discloses a group of compounds of the same class in which the substituent X is one or two halogen atoms or alkyl or alkoxy groups and Y is inter alia an alkyl group substituted with one or more halogen atoms and R is 3-phenoxybenzyl.

U.K. Patent Application No. 2,025,407 discloses a similar group of compounds in which R is a 2,6-dihalobenzyl group. Neither of these references, however, discloses any specific compounds in which the group Y is a halogenated alkyl group.

The present invention provides new compounds of the general formula (I)

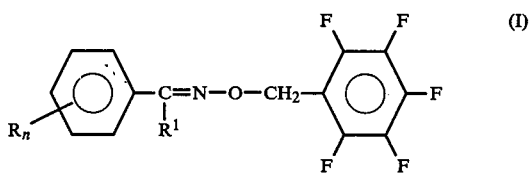

wherein
R represents F, Cl, Br, I, ethoxy, methoxy or propoxy and n is an integer between 1 and 5; or
R represents 3,4-methylenedioxy; and
R$^1$ represents di- or trichloromethyl.

Preferred compounds are those where n=1 and R is in the 4-position on the phenyl ring.

The compounds of formula I can exist in two possible isomeric forms known as E and Z. Both isomeric forms are included in the invention.

The results of tests of insecticidal activity indicate that one isomeric form has significantly greater activity than the other and that the more active form is probably the E isomer.

The more active isomers of compounds of the formula (I) are distinguished by a powerful insecticidal and acaricidal activity which is surprisingly better than that of the previously known products which have an analogous structure and the same type of action.

In particular the compounds show powerful activity against the sheep blowfly (*Lucilia cuprina*).

The invention also provides a method for the production of the compounds of the formula I in which the appropriately substituted ketone of formula II

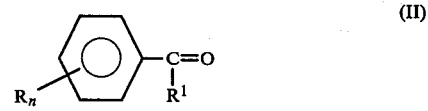

wherein R, n and R$^1$ are as defined above is reacted with O-(pentafluorobenzyl)-hydroxylamine hydrochloride.

This reaction is relatively slow but in some instances may be appreciably accelerated by using temperatures above room temperature. In general the reaction is conveniently carried out by stirring the reactants at the selected temperature and at atmospheric pressure.

The O-(pentafluorobenzyl)hydroxylamine hydrochloride can be synthesized from N-hydroxy-phthalimide, pentafluorobenzyl bromide, n-butylamine and HCl by the method of Kaztreiner, Szilagyi, Kosary and Huszti described in *Acta Chemica Academiae Scientarum Hungaricae*, 1975, 80, 167–180. The pentafluorobenzyl bromide is known and can be prepared by reacting pentafluorobenzyl alcohol with hydrobromic acid (Barbour, Buxton, Coe, Stephens and Tatlow, *J. Chem. Soc.*, 1961, 808–817) or PBr$_3$.

When R$^1$ is CCl$_3$ the above-described synthetic method gives a single stable isomer which is insecticidally active; this is surprising and apparently unique. When R$^1$ is CHCl$_2$ it appears that the proportion of isomers first formed is quite different from the equilibrium value reached after some time.

In some compounds the inactive isomer can be partly converted to the active isomer by gently heating it in a polar solvent, e.g. methanol. The isomers can be separated by any conventional method, e.g., chromatography (HPLC).

The active compounds are well tolerated by plants, have a favourable level of toxicity to warm-blooded animals, and can be used for combining arthropod pests, especially insects or acarids, which are encountered in agriculture, in veterinary practice, in forestry, in the protection of stored products and of materials, and in the hygiene field. They are active against normally sensitive and resistant species and against all or some stages of development. The abovementioned pests include *Lucilia cuprina, Musca domestica, Spodoptera litura, Plutella xylostella, Myzus persicase, Tetranychus urticae, Nephotettix cincticeps, Blatella germanica, Tribolium castaneum* and *Culex pipiens pallens*.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents.

In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxy ethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs.

The formulations in general contain from 0.1 to 95 percent by weight of active compound, preferably from 0.5 to 90 percent by weight.

The active compounds according to the invention may be used in the form of formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthoropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a methof of freeing or protecting domesticated animals from parasitical insects or acarids which comprises applying to said animals a compound according to the present invention, in admixture with a diluent or carrier.

Compounds of the formula I are also combined particularly advantageously with substances which have a synergistic or intensifying effect on pyrethroids.

Generally such substances are of the class of microsomal oxidase inhibitors i.e., they inhibit the detoxification of insecticides in insects produced by the action of oxidative enzymes.

Examples of such compounds are, inter alia, piperonyl butoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulphonyl)-propyl)-benzene.

Piperonyl butoxide is particularly useful as a potentiator. The amount of piperonyl butoxide used may vary from 1/100th to fifty times the weight of the compound I the preferred range being from about 1/100th to five parts by weight. 'Sesamex' also is a useful potentiator in similar amounts.

Examples of formulations in accordance with the invention are as follows: (parts are by weight):

Dusts:

The following substances are used to produce (a) a 5% dust and (b) a 2% dust:

(a) 5 parts of active substance,
95 parts of talcum;
(b) 2 parts of active substance,
1 part of highly dispersed silicic acid,
97 parts of talcum.

The active substance is mixed and ground with the carriers.

Granulate

The following ingredients are used to produce a 5% granulate:

5 parts of active substance,
0.25 part of epichlorohydrin,
0.25 parts of cetyl polyglycol ether,
3.50 parts of polyethylene glycol,
91 parts of kaolin The active substance is mixed with epichlorohydrin and dissolved with 6 parts of acetone, the polyethylene glycol and cetyl polyglycol ether are then added. The solution obtained is sprayed onto kaolin and the acetone is evaporated off in vacuo.

Wettable powder

The following constituents are used to produce (a) a 40%, (b) and (c) a 25%, and (d) a 10% wettable powder:

(a) 40 parts of active substance,
5 parts of sodium lignin sulphonate,
1 part of sodium dibutyl-naphthalene sulphonate,
54 parts of silicic acid;

(b) 25 parts of active substance,
4.5 parts of calcium lignin sulphonate,
1.9 parts of chalk/hydroxyethyl cellulose mixture (1:1),
1.5 parts of sodium dibutyl-naphthalene sulphonate,
19.5 parts of silicic acid,
19.5 parts of chalk,
28.1 parts of kaolin;

(c) 25 parts of active substance,
2.5 parts of isooctylphenoxy-polyoxyethyleneethanol,
1.7 parts of chalk/hydroxyethyl cellulose mixture (1:1),
8.3 parts of sodium aluminium silicate,
16.5 parts of kieselguhr,
46 parts of kaolin;

(d) 10 parts of active substance,
3 parts of a mixture of the sodium salts of saturated fatty alcohol sulphates,
5 parts of naphthalenesulphonic acid/formaldehyde condensate,
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable Concentrates

The following substances are used to produce (a) a 10%, (b) a 25%, and (c) a 50% emulsifiable concentrate:

(a) 10 parts of active substance,
3.4 parts of epoxidised vegetable oil,
3.4 parts of a combination emulsifier consisting of fatty alcohol polyglycol ether and alkylaryl-sulphonate calcium salt,
40 parts of dimethylformamide,
43.2 parts of xylene;

(b) 25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

(c) 50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the required concentration can be prepared from these concentrates by dilution with water.

Spray

The following constituents are used to produce (a) a 5% spray, (b) a 95% spray, and (c) a synergised 4% spray.

(a) 5 parts of active substance,
1 part of epichlorohydrin,
94 parts of ligroin (boiling limits 160°–190° C.);

(b) 95 parts of active substance,
5 parts of epichlorohydrin;

(c) 4 parts of active substance,
1 part of piperonyl butoxide,
79 parts of deodorised kerosene,
16 parts of alkylated naphthalene.

The following preparative examples show the preparation of compounds in accordance with the invention. The O-(pentafluorobenzyl)-hydroxylamine hydrochloride used was prepared as follows:

(a) N-(pentafluorobenzyloxy)phthalimide

N-hydroxyphthalimide (8.15 g, 0.05 mol) was dissolved in a mixture of dry dimethoxyethane (40 ml) and dry dimethyl sulphoxide (10 ml). To this solution was added, in one portion, potassium carbonate (3.46 g, 0.05 mol). An orange suspension resulted. The pentafluorobenzyl bromide (10.8 g, 0.05 mol) in dry dimethoxyethane (10 ml) was added dropwise over 1 h at room temperature. The reaction mixture was stirred at room temperature for 64 h and then quenched by pouring into water (1 l). The resulting slurry was filtered, the crystals washed with water and dried in vacuo to give N-(pentafluorobenzyloxy)phthalimide as white crystals (15.9)g.

(b) O-(pentafluorobenzyl)hydroxylamine hydrochloride

N-(Pentafluorobenzyloxy)phthalimide 15.9 g, 46 mmol), n-butylamine (3.7 g, 50 mmol) and absolute ethanol (90 ml) were placed in a dry flask under a nitrogen atmosphere. This reaction mixture was stirred at 60° C. for 1 hour, cooled and adjusted to pH 3 using dry hydrogen chloride gas. The resulting white precipitate was filtered and the crystals washed with ice-cold ethanol/ether (1:1). The filtrate was concentrated to give a second crop of crystals. The combined yield of the hydroxylamine hydrochloride was 11.15 g, 99%, m.p. (sublimed) 150°. Analysis: (Found: C, 33.7; H. 2.2; Cl, 13.9; F, 37.8; N, 5.7, $C_7H_5ClF_5NO$ requires C, 33.7; H, 2.0; Cl, 14.2; F, 38.1; N, 5.6%).

General Oxime ether preparation

Equimolar quantities of the ketone and the O-(pentafluorobenzyl)-hydroxylamine hydrochloride were dissolved in dry methanol (1.3 l/mol) and stirred at the selected temperature. The reaction was monitored by thin layer or high pressure liquid chromatography and stopped when a satisfactory yield of product had been formed. Where the product was crystalline, it was isolated by filtration and purified by recrystallization. For oily products the methanol was removed in vauco and the residue chromatographed on silica gel to yield the oxime ether.

The general method was used to make the following compounds.

EXAMPLE 1

Dichloromethyl(4-chlorophenyl), methanone-O-(2,3,4,5,6-pentafluorobenzyl)-oxime.

Analysis:

Found: C, 43,2; H, 1.8; Cl, 25.6; F, 22.2; N, 3.5. $C_{15}H_7Cl_3F_5NO$ requires C, 43.0; H, 1.7; C;, 25.4; F, 22.7; N, 3.4%, m.p. 91.6° C. NMR spectral analysis indicated that the product was a 60/40 mixture of Z and E isomers.

EXAMPLE 2

Trichloromethyl(4-ethoxyphenyl), methanone-O-(2,3,4,5,6-pentafluorobenzyl)-oxime Analysis Found: C, 44.2; H, 2.6; Cl, 23.0; F, 20.2; N, 3.2%.

$C_{17}H_{11}Cl_3F_5NO_2$ requires C, 44.1; H, 2.4; Cl, 23.0; F, 20.5; N, 3.0%, m.p. 114° C. NMR spectral analysis indicated that only one of the two possible geometric isomers of the title compound had been isolated

EXAMPLE 3

Dichloromethyl(4-ethoxyphenyl), methanone-O-(2,3,4,5,6-pentafluorobenzyl)oxime

Analysis
Found: C, 48.08, H, 3.13; Cl, 17.0; F, 21.8; N, 2.93%.
$C_{17}H_{12}Cl_2F_5NO$ requires: C, 47.69; H, 2.82; Cl, 16.56; F, 22.18; N, 3.27%.
m.p. 51.8° C.

NMR spectral analysis indicated that isolated product was a mixture of isomers Z/E=40/60. They were separated by HPLC for activity testing.
m.p. E isomer: 89.2° C.

EXAMPLE 4

Trichloromethyl(4-chlorophenyl), methanone-O-(2,3,4,5,6-pentafluorobenzyl)oxime
Analysis
Found: C, 40.05; H, 1.48; Cl, 31.3; F, 20.6; N, 3.02%.
$C_{15}H_6Cl_4F_5NO$ requires: C, 39.77; H, 1.34; Cl, 31.30. F, 20.97; N, 3.09%.
m.p. 80.1° C.
b.p. 135° C. at 0.2 mm Hg NMR spectral analysis indicated that only one of the two possible geometric isomers of the title compound had been isolated.

EXAMPLE 5

Dichloromethyl(4-bromophenyl), methanone-O-(2,3,4,5,6-pentafluorobenzyl)oxime

NMR spectral analysis indicated that the isolated product was a mixture of isomers Z/E=50/50 B.pt. 175° C. at 0.2 mm Hg pressure. The isomers were separated by HPLC for activity testing.

Analysis Found: C, 39.2 H, 1.6, N, 3.2, Br 17.7, Cl 15.7 F 20.2%;

$C_{15}H_7BrCl_2F_5NO$, requires: C, 38.9, H 1.52, N, 3.03 Br 17.3, Cl 15.3, F 20.5%.

EXAMPLE 6

Insecticidal Activity

Insecticidal activity was investigated against blowfly, *Lucilia cuprina*. The method used was as follows:

(a) The compounds were tested for activity against a susceptible strain which had been collected in the field.

The test compound was applied in acetone solution, 0.5 μl dispensed with a Drummond micropipette to the dorsum of the thorax of 2-3 day old females. Adult flies were fed on water and sugar-only and maintained at 25° C. and 60-70% RH. The mortalities were determined after 48 hours. Moribund flies were regarded as dead. The LD$_{50}$ values, in terms of concentration, were interpolated from a probit/log dose graph using a computer program.

(b) Potentiation

The compound was also tested on the insects described above in conjunction with the potentiator piperonyl butoxide by pretreating each insect with 1 μl of a 2% solution of the potentiator in acetone.

The mortalities were counted at 48 hours after treatment and compared with acetone and acetone/potentiator controls.

The LD$_{50}$ vale was determined as described above.

About the same levels of potentiation were obtained when piperonyl butoxide was replaced by an equal amount of 'Sesamex'.

Using the above-described techniques, LD$_{50}$ values were determined on each of the compounds listed in Table 1.

Comparative tests were also carried out on a commercially available synthetic pyrethroid insecticide "Permethrin", i.e., the 3'-phenoxybenzyl ester of 3-(2',2'-dichlorovinyl)-2,2-dimethylcyclo-propane carboxylic acid.

For ease of comparison the results obtained are expressed in Table 1, in terms of a "potency index" given by $$\text{Potency Index} = \frac{LD_{50} \text{ for Permethrin}}{LD_{50} \text{ for test compound}} \times \frac{100}{1}$$

The LD$_{50}$ for permethrin was determined concurrently with the LD$_{50}$ for the test compound.

TABLE 1

| Example No. | R | R' | E Isomer % | Potency Index Compound alone | Potency Index Synergised |
|---|---|---|---|---|---|
| 1 | Cl | CHCl$_2$ | 50 | 5 | 13 |
| 2 | EtO | CCl$_3$ | 100 | 185 | 290 |
| 3 | EtO | CHCl$_2$ | 100 | 200 | 430 |
| 4 | Cl | CCl$_3$ | 100 | 5 | 10 |
| 5 | Br | CHCl$_2$ | 100 | 7 | 15 |
| Permethrin | | | | 100 | — |

We claim:

1. A compound having the following formula (I)

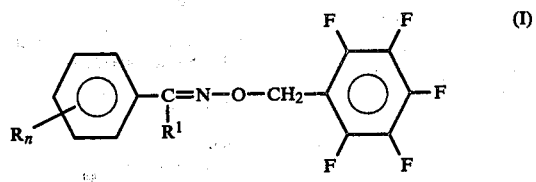

wherein R represent F, Cl, Br, I, ethoxy, methoxy or propoxy and n is an integer between 1 and 5; or R represents 3,4-methylenedioxy; and R$^1$ represents di- or trichloromethyl.

2. A compound as claimed in claim 1, wherein n is 1.

3. A compound as claimed in claim 2, wherein R is in the 4-position on the phenyl ring.

4. A compound as claimed in claim 3, wherein R is ethoxy.

5. A compound as claimed in claim 1 of the formula I in the E isomeric form.

6. Trichloromethyl(4-ethoxyphenyl)-methanono-O-(2,3,4,5,6-pentafluorobenzyl)-oxime.

7. Dichloromethyl(4-ethoxyphenyl)-methanone-O-(2,3,4,5,6-pentafluorobenzyl)-oxime.

8. Trichloromethyl(4-chlorophenyl)-methanone-O-(2,3,4,5,6-pentafluorobenzyl)-oxime.

9. Dichloromethyl(4-chlorophenyl)-methanone-O-(2,3,4,5,6-pentafluorobenzyl)-oxime.

10. Dichloromethyl(4-bromophenyl)-methanone-O-(2,3,4,5,6-pentafluorobenzyl)-oxime.

11. An arthropodicidal composition containing as active ingredient an effective amount of the compound of claim 1 in admixture with a diluent or carrier.

12. A method of combating arthropods which comprises applying to the arthropods, or to a habitat thereof, an effective amount of the compound of claim 1.

13. A method of combating arthoropods which comprises applying to the arthropods, or to a habitat thereof, an effective amount of the composition of claim 11.

14. A method of freeing or protecting domesticated animals from parasitical insects or acarids which comprises applying to said animals an effective amount of a compound of claim 1.

15. A method of freeing or protecting domesticated animals from parasitical insects or acarids which comprises applying to said animals an effective amount of the composition of claim 11.

* * * * *